(12) United States Patent
Muller et al.

(10) Patent No.: US 11,266,589 B2
(45) Date of Patent: *Mar. 8, 2022

(54) HAIR DYEING COMPOSITION COMPRISING AN OXIDATION DYE, A SCLEROGLUCAN GUM, AND AN ALKYLPOLYGLYCOSIDE

(71) Applicant: L'OREAL, Paris (FR)

(72) Inventors: Sabrina Muller, Saint-Ouen (FR); Delphine Charrier, Saint-Ouen (FR); Cindy Yadel, Saint-Ouen (FR); Fanny Cardonnel, Saint-Ouen (FR); Mladen Milic, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/252,856

(22) PCT Filed: Jun. 20, 2019

(86) PCT No.: PCT/EP2019/066365
§ 371 (c)(1),
(2) Date: Dec. 16, 2020

(87) PCT Pub. No.: WO2019/243509
PCT Pub. Date: Dec. 26, 2019

(65) Prior Publication Data
US 2021/0128444 A1 May 6, 2021

(30) Foreign Application Priority Data
Jun. 20, 2018 (FR) ........................ 1855434

(51) Int. Cl.
| *A61Q 5/10* | (2006.01) |
| *A61K 8/73* | (2006.01) |
| *A61K 8/19* | (2006.01) |
| *A61K 8/22* | (2006.01) |
| *A61K 8/41* | (2006.01) |
| *A61K 8/49* | (2006.01) |
| *A61K 8/60* | (2006.01) |

(52) U.S. Cl.
CPC ............... *A61K 8/737* (2013.01); *A61K 8/19* (2013.01); *A61K 8/22* (2013.01); *A61K 8/41* (2013.01); *A61K 8/411* (2013.01); *A61K 8/415* (2013.01); *A61K 8/416* (2013.01); *A61K 8/4946* (2013.01); *A61K 8/602* (2013.01); *A61K 8/731* (2013.01); *A61Q 5/10* (2013.01); *A61K 2800/596* (2013.01); *A61K 2800/882* (2013.01)

(58) Field of Classification Search
CPC . A61Q 5/10; A61K 8/22; A61K 8/415; A61K 8/19; A61K 8/41; A61K 2800/882; A61K 8/416; A61K 8/731; A61K 8/73; A61K 8/602; A61K 47/38; A61K 47/61; A61K 9/2018; A61K 8/737; A61K 8/411; A61K 2800/596

USPC .......................................................... 8/405
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |

(Continued)

FOREIGN PATENT DOCUMENTS

| DE | 2359399 A1 | 6/1975 |
| DE | 3843892 A1 | 6/1990 |

(Continued)

OTHER PUBLICATIONS

International Search Report and Written Opinion for counterpart Application No. PCT/EP2019/066365, dated Aug. 13, 2019.

(Continued)

*Primary Examiner* — Eisa B Elhilo
(74) *Attorney, Agent, or Firm* — The Marbury Law Group, PLLC

(57) ABSTRACT

The disclosure relates to a composition for dyeing keratin fibers, in particular human keratin fibers such as hair, comprising one or more oxidation dyes, one or more scleroglucan gums in a total weight content greater than or equal to 0.5% relative to the total weight of the composition, and one or more and optionally one or more additional surfactants, preferably cationic surfactants. The disclosure also relates to a method for dyeing keratin fibers using said composition and to a multi-compartment device suitable for implementing said composition.

20 Claims, No Drawings

(56) References Cited

U.S. PATENT DOCUMENTS

| | | | |
|---|---|---|---|
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,137,180 A | 1/1979 | Naik et al. | |
| 4,157,388 A | 6/1979 | Christiansen | |
| 4,165,367 A | 8/1979 | Chakrabarti | |
| 4,172,887 A | 10/1979 | Vanlerberghe et al. | |
| 4,217,914 A | 8/1980 | Jacquet et al. | |
| 4,240,450 A | 12/1980 | Grollier et al. | |
| 4,349,532 A | 9/1982 | Vanlerberghe et al. | |
| 4,381,919 A | 5/1983 | Jacquet et al. | |
| 4,591,610 A | 5/1986 | Grollier | |
| 4,702,906 A | 10/1987 | Jacquet et al. | |
| 4,719,282 A | 1/1988 | Nadolsky et al. | |
| 4,761,273 A | 8/1988 | Grollier et al. | |
| 4,839,166 A | 6/1989 | Grollier et al. | |
| 4,874,554 A | 10/1989 | Lange et al. | |
| 4,996,059 A | 2/1991 | Grollier et al. | |
| 5,061,289 A | 10/1991 | Clausen et al. | |
| 5,089,252 A | 2/1992 | Grollier et al. | |
| 5,180,397 A | 1/1993 | Grollier et al. | |
| 5,180,399 A | 1/1993 | Grollier et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,099,592 A | 8/2000 | Vidal et al. | |
| 2003/0229948 A1 | 12/2003 | Desenne et al. | |
| 2004/0034946 A1 | 2/2004 | Legrand et al. | |
| 2004/0060125 A1 | 4/2004 | Audouset | |
| 2004/0064901 A1 | 4/2004 | Kleen et al. | |
| 2004/0133993 A1 | 7/2004 | Cottard et al. | |
| 2004/0172771 A1 | 9/2004 | Cottard et al. | |
| 2004/0221401 A1* | 11/2004 | Desenne | A61K 8/365 8/405 |
| 2005/0039270 A1* | 2/2005 | Legrand | A61K 8/44 8/405 |
| 2006/0117493 A1 | 6/2006 | Bureiko et al. | |
| 2006/0182697 A1* | 8/2006 | Lalleman | A61Q 17/04 424/59 |
| 2008/0282481 A1 | 11/2008 | De Boni et al. | |
| 2010/0175202 A1 | 7/2010 | Simonet et al. | |
| 2010/0192969 A1* | 8/2010 | DeGeorge | A61K 8/23 132/208 |
| 2010/0199441 A1 | 8/2010 | Hercouet et al. | |
| 2011/0150797 A1 | 6/2011 | Legrand et al. | |
| 2011/0203605 A1* | 8/2011 | Allard | A61K 8/23 132/208 |
| 2011/0203606 A1 | 8/2011 | Recchion et al. | |
| 2011/0209720 A1 | 9/2011 | DeGeorge et al. | |
| 2012/0076930 A1 | 3/2012 | Miller | |
| 2012/0210523 A1 | 8/2012 | Lalleman et al. | |
| 2013/0042883 A1 | 2/2013 | DeGeorge et al. | |
| 2013/0167862 A1 | 7/2013 | Lopez et al. | |
| 2014/0082855 A1 | 3/2014 | Rapold et al. | |
| 2014/0305464 A1 | 10/2014 | DeGeorge et al. | |
| 2014/0326270 A1 | 11/2014 | DeGeorge et al. | |
| 2015/0143637 A1 | 5/2015 | Rapold et al. | |
| 2015/0335545 A1 | 11/2015 | Rapold et al. | |
| 2016/0279036 A1 | 9/2016 | Schoepgens et al. | |
| 2017/0172901 A1 | 6/2017 | Kerl et al. | |
| 2017/0354584 A1 | 12/2017 | Lalleman et al. | |

FOREIGN PATENT DOCUMENTS

| | | | |
|---|---|---|---|
| DE | 4133957 A1 | 4/1993 | |
| DE | 19543988 A1 | 5/1997 | |
| EP | 0080976 A1 | 6/1983 | |
| EP | 0122324 A1 | 10/1984 | |
| EP | 0337354 A1 | 10/1989 | |
| EP | 0770375 A1 | 5/1997 | |
| FR | 1492597 A | 8/1967 | |
| FR | 1583363 A | 10/1969 | |
| FR | 2077143 A5 | 10/1971 | |
| FR | 2080759 A1 | 11/1971 | |
| FR | 2162025 A | 7/1973 | |
| FR | 2190406 A2 | 2/1974 | |
| FR | 2252840 A1 | 6/1975 | |
| FR | 2270846 A1 | 12/1975 | |
| FR | 2280361 A2 | 2/1976 | |
| FR | 2316271 A1 | 1/1977 | |
| FR | 2320330 A1 | 3/1977 | |
| FR | 2336434 A1 | 7/1977 | |
| FR | 2368508 A2 | 5/1978 | |
| FR | 2383660 A1 | 10/1978 | |
| FR | 2393573 A1 | 1/1979 | |
| FR | 2413907 A1 | 8/1979 | |
| FR | 2470596 A1 | 6/1981 | |
| FR | 2505348 A1 | 11/1982 | |
| FR | 2519863 A1 | 7/1983 | |
| FR | 2542997 A1 | 9/1984 | |
| FR | 2598611 A1 | 11/1987 | |
| FR | 2618070 A1 | 1/1989 | |
| FR | 2633940 A1 | 7/1991 | |
| FR | 2733749 A1 | 11/1996 | |
| FR | 2801308 A1 | 5/2001 | |
| FR | 2886136 A1 | 12/2006 | |
| FR | 3008615 A1 | 1/2015 | |
| GB | 1026978 A | 4/1966 | |
| GB | 1153196 A | 5/1969 | |
| GB | 1546809 A | 5/1979 | |
| GB | 2207443 A * | 2/1989 | ............... A61Q 5/10 |
| JP | 02-019576 A | 1/1990 | |
| JP | 05-163124 A | 6/1993 | |
| WO | 94/08969 A1 | 4/1994 | |
| WO | 94/08970 A1 | 4/1994 | |
| WO | 96/15765 A1 | 5/1996 | |
| WO | 2016/091816 A1 | 6/2016 | |
| WO | 2018/056235 A1 | 3/2018 | |
| WO | 2019/243505 A1 | 12/2019 | |
| WO | 2019/243507 A1 | 12/2019 | |
| WO | 2019/243508 A1 | 12/2019 | |
| WO | 2019/243511 A1 | 12/2019 | |
| WO | 2019/243512 A1 | 12/2019 | |
| WO | 2019/243513 A1 | 12/2019 | |

OTHER PUBLICATIONS

International Search Report and Written Opinion for counterpart Application No. PCT/EP2019/066368, dated Sep. 3, 2019.

International Search Report and Written Opinion for counterpart Application No. PCT/EP2019/066363, dated Sep. 2, 2019.

International Search Report and Written Opinion for counterpart Application No. PCT/EP2019/066369, dated Aug. 22, 2019.

International Search Report and Written Opinion for counterpart Application No. PCT/EP2019/066364, dated Sep. 11, 2019.

International Search Report and Written Opinion for counterpart Application No. PCT/EP2019/066361, dated Aug. 22, 2019.

International Search Report and Written Opinion for counterpart Application No. PCT/EP2019/066370, dated Sep. 11, 2019.

Mintel, "Root Vanish," Kazumi, ID 3319563, XP055562798, dated Feb. 27, 2015.

Mintel, "Colourant Cream," LG Household and Health Care, ID 1533817, XP055547325, dated May 11, 2011.

Mintel, "Hair Colourant," Garnier, ID 644332, XP055547333, dated Jan. 16, 2007.

Non-Final Office Action for copending U.S. Appl. No. 17/252,883, dated Aug. 18, 2021.

Non-Final Office Action for copending U.S. Appl. No. 17/253,035, dated Aug. 20, 2021.

Non-Final Office Action for copending U.S. Appl. No. 17/253,007, dated Aug. 25, 2021.

Non-Final Office Action for copending U.S. Appl. No. 17/252,870, dated Sep. 10, 2021.

Non-Final Office Action for copending U.S. Appl. No. 17/252,974, dated Sep. 20, 2021.

(56) References Cited

OTHER PUBLICATIONS

Non-Final Office Action for copending U.S. Appl. No. 17/253,019, dated Sep. 24, 2021.
Final Office Action for copending U.S. Appl. No. 17/252,974, dated Dec. 29, 2021.

\* cited by examiner

HAIR DYEING COMPOSITION COMPRISING AN OXIDATION DYE, A SCLEROGLUCAN GUM, AND AN ALKYLPOLYGLYCOSIDE

CROSS REFERENCE TO RELATED APPLICATION

This is a national stage application of PCT/EP2019/066365, filed internationally on Jun. 20, 2019, which claims priority to French Application No. 1855434, filed on Jun. 20, 2018, both of which are incorporated by reference herein in their entireties.

The present invention relates to the field of dyeing keratin fibers and more particularly to the field of hair dyeing.

Among the methods for dyeing human keratin fibers, such as the hair, mention may be made of oxidation dyeing or permanent dyeing. More particularly, this form of dyeing uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colorless or weakly colored compounds which, when combined with oxidizing products, can give access to colored species.

The shades obtained with these oxidation bases are quite often varied by combining them with one or more couplers, these couplers being notably chosen from aromatic meta-diamines, meta-aminophenols, meta-diphenols and certain heterocyclic compounds such as indole compounds.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloring, via an oxidative condensation reaction between the oxidation dyes.

Oxidation dyeing must moreover satisfy a certain number of requirements. Thus, it must be free of toxicological drawbacks, it must enable shades to be obtained in the desired intensity and it must show good persistence in the face of external attacking factors such as light, bad weather, washing, permanent waving, perspiration and rubbing.

The dyeing process must also make it possible to cover gray hair and, finally, must be as unselective as possible, i.e. it must produce the smallest possible color differences along the same keratin fiber, which generally includes areas that are differently sensitized (i.e. damaged) from its end to its root, so as to obtain the most uniform coloring possible of the keratin fibers. Dye compositions must also give good cosmetic properties to keratin fibers, in particular care, softness and/or hold, and must have good working qualities, in particular they must be easy to apply, while at the same time achieving visible (i.e. notably intense, chromatic), uniform and fast coloring results.

The compositions used in a dyeing process must also have good mixing and application properties on keratin fibers, and notably good rheological properties so as not to run down the face, onto the scalp or beyond the areas that it is proposed to dye, when they are applied; this notably allows uniform application from the roots to the ends.

The composition according to the invention also shows very good stability over time for several weeks.

In particular, it is sought to obtain dye compositions that are stable over time for several weeks. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage.

Specifically, it is desirable for the dye compositions to be stable over time, in particular stable after 1 month at 45° C., or even after 2 months at 45° C.

It is also sought to obtain dye compositions that are stable over a wide pH range and in particular with respect to extreme pH values, for example to alkaline pH values ranging from 9 to 12. Finally, the dye compositions may occasionally be destabilized (undergo phase separation) by high contents of certain compounds, for instance on account of their high content of certain compounds, and it is thus desirable for these compositions to be stable under these conditions, in particular for them not to undergo phase separation.

These aims and others are achieved by the present invention, one subject of which is thus a composition (A) for dyeing keratin fibers, preferably human keratin fibers such as the hair, comprising:
  one or more oxidation dyes;
  one or more scleroglucan gums in a total content of greater than or equal to 0.5% by weight relative to the weight of the composition; and
  one or more nonionic surfactants chosen from alkyl(poly)glycosides;
  and optionally one or more additional surfactants, preferably cationic surfactants.

Another subject of the invention relates to a ready-to-use composition for dyeing keratin fibers, in particular human keratin fibers such as the hair, obtained after mixing a composition (A) comprising:
  one or more oxidation dyes;
  one or more scleroglucan gums in a total amount of greater than or equal to 0.5% by weight relative to the total weight of the composition;
  one or more nonionic surfactants chosen from alkyl(poly)glycosides;
  and optionally one or more additional surfactants, preferably cationic surfactants;
  and a composition (B) comprising
  one or more chemical oxidizing agents.

For the purposes of the invention, the term "ready-to-use" refers to any composition that is intended to be applied immediately to keratin fibers.

The invention is also directed toward a process for dyeing keratin fibers, and in particular human keratin fibers such as the hair, involving the application to the fibers of a dye composition (A) as defined previously, and of an oxidizing composition (B) comprising at least one chemical oxidizing agent, preferably chosen from hydrogen peroxide and/or one or more systems for generating hydrogen peroxide, preferably from hydrogen peroxide, the oxidizing composition (B) being mixed with the dye composition just before use (application to said fibers) (extemporaneously) or at the time of use, or alternatively the dye composition and oxidizing composition being applied sequentially without intermediate rinsing.

A subject of the invention is also a multi-compartment device (or "kit") for implementing the composition for dyeing keratin fibers, preferably comprising at least two compartments, a first compartment containing the dye composition (A) as defined previously, and the second compartment containing at least one oxidizing composition (B) comprising at least one chemical oxidizing agent, preferably chosen from hydrogen peroxide and/or one or more systems for generating hydrogen peroxide, preferably from hydrogen peroxide, the compositions in the compartments being intended to be mixed before application, to give the formulation after mixing; in particular, the kit may be an aerosol device.

For the purposes of the present invention, the term "composition for dyeing" or "dye composition" means a composition intended to be applied to keratin fibers, preferably human keratin fibers and in particular the hair, optionally after mixing with an oxidizing composition comprising at least one chemical oxidizing agent. For the purposes of the present invention, the term "ready-to-use dye composition" or "ready-to-use composition" means a composition resulting from mixing a dye composition and an oxidizing composition. The ready-to-use dye composition may be prepared just before application to said keratin fibers.

The compositions according to the invention can thus give very good dyeing performance on keratin fibers, notably in terms of build-up, intensity, chromaticity and/or selectivity. They also afford compositions which have good rheological properties so as not to run down onto the face, the scalp or beyond the areas that it is proposed to dye, when they are applied.

The compositions according to the invention are stable. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage. In particular, it is desirable for the dye compositions to be stable over time, in particular stable after 1 month at 45° C., or even after 2 months at 45° C.

Furthermore, the compositions according to the invention have the advantage of being stable (of not undergoing phase separation) independently of the pH value and in particular with respect to extreme pH values, notably at an alkaline pH value of greater than or equal to 9, for example at alkaline pH values ranging from 9 to 12. Finally, the compositions are preferably stable (do not undergo phase separation), even in the presence of a high content of certain compounds, for instance oxidation dyes and/or cationic compounds such as cationic polymers, and it is thus desirable for these compositions to be stable under these conditions, in particular for them not to undergo phase separation.

Moreover, the compositions of the invention are advantageously translucent, which gives them a visual appearance that the consumer finds esthetic and attractive, and can contribute toward styling effects, which may be reflected in terms of contribution.

Other features and advantages of the invention will emerge more clearly on reading the description and the examples that follow.

In the text hereinbelow, unless otherwise indicated, the limits of a range of values are included in that range, notably in the expressions "between" and "ranging from . . . to . . . ".

The keratin fibers are preferably human keratin fibers, preferably the hair.

The expression "at least one" is equivalent to the expression "one or more".

Advantageously, the composition according to the invention has a thickened texture, and is in cream or gel form, preferably in gel form, and the composition is preferably translucent.

Thus, the composition according to the invention generally has, at room temperature (25° C.), a viscosity of greater than 50 cps, preferably between 200 and 100 000 cps, more preferentially between 500 and 50 000 cps, even more preferentially between 800 and 10 000 cps, and better still from 1000 to 8000 cps measured at 25° C. at a spin speed of 200 rpm using a rheometer such as the Rheomat RM 180 equipped with a No. 3 or 4 spindle, the measurement preferably being taken after 60 seconds of rotation of the spindle (after which time stabilization of the viscosity and of the spin speed of the spindle is observed).

Oxidation Dyes

The composition according to the invention comprises one or more oxidation dyes.

The oxidation dye precursors that may be used in the present invention are generally chosen from oxidation bases, optionally combined with one or more couplers.

The oxidation bases may preferably be chosen from para-phenylenediamines, bis(phenyl)alkylenediamines, para-aminophenols, ortho-aminophenols and heterocyclic bases, and the addition salts thereof.

Preferentially, the oxidation base(s) of the invention are chosen from para-phenylenediamines and heterocyclic bases. Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, 2-methoxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and 2-methoxymethyl-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(J-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, mention may be made in particular of pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308.

Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and also the addition salts thereof.

More particularly, the oxidation bases according to the invention are chosen from 3-aminopyrazolo[1,5-a]pyridines preferably substituted in position 2 with:

a) a (di)($C_1$-$C_6$)(alkyl)amino group, the alkyl groups possibly being substituted with one or more hydroxyl, amino or imidazolium groups;

b) a cationic or non-cationic 5- to 7-membered heterocloalkyl group comprising from 1 to 3 heteroatoms, optionally substituted with one or more ($C_1$-$C_6$)alkyl groups such as di($C_1$-$C_4$)alkylpiperazinium;

c) a ($C_1$-$C_6$)alkoxy group optionally substituted with one or more hydroxyl groups, such as O-hydroxyalkoxy, and also the addition salts thereof.

Among the pyrimidine derivatives, mention may be made of the compounds described, for example, in patents DE 2359399, JP 88169571, JP 05-63124 and EP 0/770/375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof preferably, the heterocyclic oxidation bases of the invention are chosen from 4,5-diaminopyrazoles such as 4,5-diamino-1-(β-hydroxyethyl)pyrazole. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl) pyrazole and/or a salt thereof.

Pyrazole derivatives that may also be mentioned include diamino-N,N-dihydropyrazolopyrazolones and notably those described in patent application FR-A-2 886 136, such as the following compounds and the addition salts thereof. 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a] pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a] pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1, 2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

As heterocyclic bases, use will preferentially be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidation base(s) used in the context of the invention are generally present in an amount ranging from 0.001% to 10% by weight approximately, and preferably ranging from 0.005% to 5%, relative to the total weight of the dye composition.

The additional couplers that are conventionally used for the dyeing of keratin fibers are preferably chosen from meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2-methyl-5-aminophenol, 3-amino-2-chloro-6-methylphenol, 2-methyl-5-hydroxyethylaminophenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, thymol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(p-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are notably chosen from the addition salts with an acid, such as hydrochlorides, hydrobromides, sulfates, citrates, succinates, tartrates, lactates, tosylates, benzenesulfonates, phosphates and acetates.

In the context of the present invention, when they are present, the coupler(s) are generally present in a total amount ranging from 0.001% to 10% by weight approximately of the total weight of the dye composition, and preferably ranging from 0.005% to 5% by weight relative to the total weight of the dye composition.

Preferably, the total content of oxidation dyes in the composition according to the invention is between 0.001% and 20% by weight, preferably between 0.001% and 10% by weight, preferably between 0.01% and 5% by weight, relative to the weight of the composition.

The composition according to the invention preferably comprises at least one oxidation base and at least one coupler.

Scleroglucan Gums

According to the invention, the composition comprises one or more scleroglucan gums in a total content of greater than or equal to 0.5% by weight relative to the weight of the composition.

Scleroglucan gums are polysaccharides of microbial origin produced by a fungus of *Sclerotium* type, in particular *Sclerotium rolfsii*. They are polysaccharides constituted solely of glucose units.

Scleroglucan gums may or may not be modified. Preferably, the scleroglucan gums used in the present invention are unmodified.

Examples of scleroglucan gums that may be used in the present invention are, in a nonlimiting manner, the products sold under the name Actigum CS, in particular Actigum CS 11 by the company Sanofi Bio Industries and under the name Amigum or Amigel by the company Alban Müller International.

Other scleroglucan gums, such as the gum treated with glyoxal described in French patent application No. 2 633 940, may also be used.

The scleroglucan gum(s) that may be used according to the invention preferably represent a total content ranging from 0.5% to 10% by weight, more preferentially from 0.5% to 5% by weight, even more preferentially from 0.5% to 3% by weight and better still 0.5% to 2% by weight relative to the total weight of the composition, preferably from 0.7% to 1.5% by weight.

Alkyl(Poly)Glycoside Surfactants

Composition (A) according to the invention comprises one or more nonionic surfactants chosen from alkyl(poly)glycosides.

The term "alkyl(poly)glycosides" means alkylmonoglycosides and/or alkylpolyglycosides.

Preferably, the nonionic surfactants of alkyl(poly)glycoside type are represented by the following general formula:

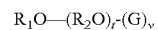

in which:
- $R_1$ represents a linear or branched alkyl or alkenyl radical including 6 to 24 carbon atoms and notably 8 to 18 carbon atoms, or an alkylphenyl radical of which the linear or branched alkyl radical includes 6 to 24 carbon atoms and notably 8 to 18 carbon atoms,
- $R_2$ represents an alkylene radical including 2 to 4 carbon atoms,
- G represents a sugar unit including 5 to 6 carbon atoms,
- t denotes a value ranging from 0 to 10 and preferably from 0 to 4,
- v denotes a value ranging from 1 to 15 and preferably from 1 to 4.

Preferably, the alkyl(poly)glycoside surfactants are compounds of the formula described above in which:
- $R_1$ denotes a linear or branched, saturated or unsaturated alkyl radical including from 8 to 18 carbon atoms,
- $R_2$ represents an alkylene radical including 2 to 4 carbon atoms,
- t denotes a value ranging from 0 to 3 and preferably equal to 0,
- G denotes glucose, fructose or galactose, preferably glucose,
- the degree of polymerization, i.e. the value of v, possibly ranging from 1 to 15 and preferably from 1 to 4; the mean degree of polymerization more particularly being between 1 and 2.

The glucoside bonds between the sugar units are preferably of 1-6 or 1-4 type and preferably of 1-4 type.

Preferably, the alkyl(poly)glycoside surfactant is an alkyl(poly)glucoside surfactant.

Preferably, the alkyl(poly)glycoside surfactant(s) are chosen from ($C_6$-$C_{24}$ alkyl)(poly)glycosides, more preferentially from ($C_8$-$C_{18}$ alkyl)(poly)glycosides, preferably from $C_8$/$C_{16}$-alkyl(poly)glucosides, preferably of 1,4 type, and preferably chosen from decyl glucosides, cocoyl glucosides and/or caprylyl/capryl glucosides, preferably caprylyl/capryl glucosides.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, the alkyl(poly)glycoside, preferably alkyl(poly)glucoside, nonionic surfactant(s) are present in a total content ranging from 0.01% to 10%, more preferentially from 0.05% to 5% by weight and better still from 0.1% to 3% by weight relative to the total weight of the composition.

Additional Surfactants

Preferably, according to the invention, the dye composition also comprises one or more additional surfactants other than alkyl(poly)glycosides.

The additional surfactant(s) may be chosen from anionic surfactants, amphoteric or zwitterionic surfactants, cationic surfactants, and nonionic surfactants other than alkylpolyglycosides, and mixtures thereof, preferably from cationic surfactants.

According to one embodiment, the composition according to the invention comprises one or more additional surfactants chosen from nonionic surfactants other than alkylpolyglycosides.

The additional nonionic surfactants that may be used according to the invention may be chosen from:
  alcohols, α-diols and ($C_{1-20}$)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or else these compounds comprising at least one fatty chain including from 8 to 40 carbon atoms and notably from 16 to 30 carbon atoms; in particular, oxyethylenated alcohols comprising at least one saturated or unsaturated, linear or branched $C_8$ to $C_{40}$ alkyl chain, comprising from 1 to 100 mol of ethylene oxide, preferably from 2 to 50 and more particularly from 2 to 40 mol of ethylene oxide and including one or two fatty chains;
  condensates of ethylene oxide and propylene oxide with fatty alcohols;
  polyethoxylated fatty amides preferably containing from 2 to 30 ethylene oxide units, polyglycerolated fatty amides including on average from 1 to 5 and in particular from 1.5 to 4 glycerol groups;
  ethoxylated fatty acid esters of sorbitan, preferably containing from 2 to 40 ethylene oxide units;
  fatty acid esters of sucrose;
  polyoxyalkylenated, preferably polyoxyethylenated, fatty acid esters containing from 2 to 150 mol of ethylene oxide, including oxyethylenated plant oils;
  N—($C_6$-$C_{24}$ alkyl)glucamine derivatives;
  amine oxides such as ($C_{10}$-$C_{14}$ alkyl)amine oxides or N—($C_{10}$-$C_{14}$ acyl)aminopropylmorpholine oxides;
  and mixtures thereof.

According to another preferred embodiment, the composition according to the invention comprises one or more additional surfactants chosen from cationic surfactants.

Preferably, the cationic surfactant(s) are chosen from optionally polyoxyalkylenated primary, secondary or tertiary fatty amine salts, quaternary ammonium salts, and mixtures thereof.

Examples of quaternary ammonium salts that may notably be mentioned include:
  those corresponding to the general formula (X) below:

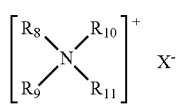

in which the groups $R_8$ to $R_{11}$, which may be identical or different, represent a linear or branched aliphatic group including from 1 to 30 carbon atoms, or an aromatic group such as aryl or alkylaryl, at least one of the groups $R_8$ to $R_{11}$ including from 8 to 30 carbon atoms and preferably from 12 to 24 carbon atoms. The aliphatic groups may include heteroatoms notably such as oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (X), preference is given, firstly, to tetraalkylammonium chlorides, for instance dialkyldimethylammonium or alkyltrimethylammonium chlorides in which the alkyl group includes from about 12 to 22 carbon atoms, in particular behenyltrimethylammonium chloride, distearyldimethylammonium chloride, cetyltrimethylammonium chloride or benzyldimethylstearylammonium chloride, or, secondly, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (XI) below:

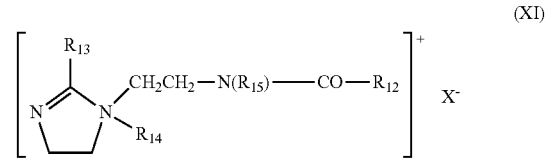

in which $R_{12}$ represents an alkenyl or alkyl group including from 8 to 30 carbon atoms, for example derived from tallow fatty acids, $R_{13}$ represents a hydrogen atom, a $C_1$-$C_4$ alkyl group or an alkenyl or alkyl group including from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, ($C_1$-$C_4$)alkyl sulfates and ($C_1$-$C_4$)alkyl- or ($C_1$-$C_4$)alkylarylsulfonates.

Preferably, $R_{12}$ and $R_{13}$ denote a mixture of alkenyl or alkyl groups including from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo, quaternary diammonium or triammonium salts, in particular of formula (XII) below:

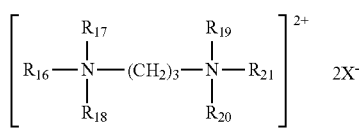
(XII)

in which $R_{16}$ denotes an alkyl group including from about 16 to 30 carbon atoms, which is optionally hydroxylated and/or interrupted with one or more oxygen atoms, $R_{17}$ is chosen from hydrogen, an alkyl group including from 1 to 4 carbon atoms or a group —$(CH_2)_3$—$N^+(R_{16a})$ $(R_{17a})(R_{18a})$, $R_{16a}$, $R_{17a}$, $R_{18a}$, $R_{18}$, $R_{19}$, $R_{20}$ and $R_{21}$, which may be identical or different, are chosen from hydrogen and an alkyl group including from 1 to 4 carbon atoms, and $X^-$ is an anion chosen from the group of halides, acetates, phosphates, nitrates, $(C_1-C_4)$alkyl sulfates, $(C_1-C_4)$alkylsulfonates and $(C_1-C_4)$alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (XIII) below:

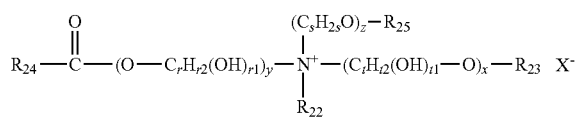
(XIII)

in which:

$R_{22}$ is chosen from $C_1-C_6$ alkyl groups and $C_1-C_6$ hydroxyalkyl or dihydroxyalkyl groups, $R_{23}$ is chosen from:
the group

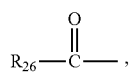

linear or branched, saturated or unsaturated $C_1-C_{22}$ hydrocarbon-based groups $R_{27}$,
a hydrogen atom,
$R_{25}$ is chosen from:
the group

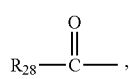

linear or branched, saturated or unsaturated $C_1-C_6$ hydrocarbon-based groups $R_{29}$,
a hydrogen atom,
$R_{24}$, $R_{26}$ and $R_{28}$, which may be identical or different, are chosen from linear or branched, saturated or unsaturated $C_7-C_{21}$ hydrocarbon-based groups, r, s and t, which may be identical or different, are integers ranging from 2 to 6,
r1 and t1, which may be identical or different, are equal to 0 or 1,
r2+r1=2 r and t1+t2=2t,
y is an integer ranging from 1 to 10,
x and z, which may be identical or different, are integers ranging from 0 to 10,
$X^-$ is a simple or complex organic or inorganic anion,
with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_1-C_{21}$ hydrocarbon-based groups, and more particularly from linear or branched, saturated or unsaturated $C_{11}-C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a $(C_1-C_4)$alkyl sulfate or a $(C_1-C_4)$alkyl- or $(C_1-C_4)$alkylarylsulfonate. However, use may be made of methanesulfonate, phosphate, nitrate, tosylate, an anion derived from an organic acid, such as acetate or lactate, or any other anion that is compatible with the ammonium bearing an ester functional group.

The anion $X^-$ is even more particularly chloride, methyl sulfate or ethyl sulfate.

Use is made more particularly, in the composition according to the invention, of the ammonium salts of formula (XIII) in which:

$R_{22}$ denotes a methyl or ethyl group,
x and y are equal to 1,
z is equal to 0 or 1,
r, s and t are equal to 2,
$R_{23}$ is chosen from:
the group

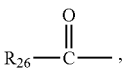

methyl, ethyl or $C_{14}-C_{22}$ hydrocarbon-based groups,
a hydrogen atom,
$R_{25}$ is chosen from:
the group

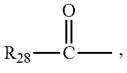

a hydrogen atom,

R$_{24}$, R$_{26}$ and R$_{28}$, which may be identical or different, are chosen from linear or branched, saturated or unsaturated C$_{13}$-C$_{17}$ hydrocarbon-based groups, and preferably from linear or branched, saturated or unsaturated C$_{13}$-C$_{17}$ alkyl and alkenyl groups.

Advantageously, the hydrocarbon-based groups are linear.

Among the compounds of formula (XIII), examples that may be mentioned include salts, notably the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may also be made of the behenoylhydroxypropyltrimethylammonium chloride sold, for example, by the company Kao under the name Quartamin BTC 131.

Preferably, the ammonium salts containing at least one ester function contain two ester functions.

Preferably, the cationic surfactant(s) are chosen from cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

When the composition according to the invention contains one or more additional surfactants, their total content preferably ranges from 0.01% to 20%, more preferentially from 0.05% to 10% by weight and better still from 0.1% to 5% by weight relative to the total weight of the composition.

Preferably, the composition according to the invention comprises one or more additional cationic surfactants in a total content preferably ranging from 0.01% to 10%, more preferentially from 0.05% to 5% by weight and better still from 0.1% to 3% by weight relative to the total weight of the composition.

Associative Polymers

The composition according to the invention may also comprise one or more associative polymers. The associative polymers according to the invention are polymers comprising at least one C$_8$-C$_{30}$ fatty chain and of which the molecules are capable, in the formulation medium, of associating with each other or with molecules of other compounds.

Preferably, the fatty chain includes from 10 to 30 carbon atoms.

A particular case of associative polymers is amphiphilic polymers, i.e. polymers including one or more hydrophilic parts which make them water-soluble and one or more hydrophobic zones (comprising at least one fatty chain) via which the polymers interact and assemble with each other or with other molecules.

The associative polymers that may be used in the composition according to the invention may be chosen from nonionic, anionic, cationic and amphoteric associative polymers, and mixtures thereof.

When they are present, the associative polymer(s), preferably nonionic associative polymers, are present in the composition in a total weight content preferably between 0.01% and 10%, even more preferentially between 0.05% and 5% of the total weight of the composition, better still between 0.1% and 2% by weight relative to the total weight of the composition.

Cationic Polymers

According to an advantageous embodiment of the invention, the composition comprises one or more cationic polymers, other than the cationic associative polymers mentioned previously.

As examples of cationic polymers that may be used in the compositions according to the invention, mention may be made in particular of:

(1) alkyldiallylamine or dialkyldiallylammonium cyclopolymers mention may be made more particularly of the dimethyldiallylammonium salt (for example chloride) homopolymer, for example sold under the name Merquat 100 by the company Nalco. Preferably, the polymers are chosen from dialkyldiallylammonium homopolymers.

(2) Quaternary Diammonium Polymers

Mention may be made more particularly of cationic polymers that are constituted of repeating units corresponding to the formula:

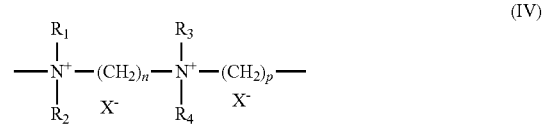

in which R$_1$, R$_2$, R$_3$ and R$_4$, which may be identical or different, denote an alkyl or hydroxyalkyl radical containing from 1 to 4 carbon atoms, n and p are integers ranging from 2 to 20, and X– is an anion derived from a mineral or organic acid.

A particularly preferred compound of formula (IV) is the one for which R$_1$, R$_2$, R$_3$ and R$_4$ represent a methyl radical and n=3, p=6 and X=Cl, known as Hexadimethrine chloride according to the INCI (CTFA) nomenclature.

Preferably, the cationic polymer(s) are chosen from dialkyldiallylammonium homopolymers, in particular homopolymers of dimethyldiallylammonium salts, poly(dimethyliminio)-1,3-propanediyl(dimethyliminio)-1,6-hexanediyl dichloride polymers, the INCI name of which is hexadimethrine chloride, and mixtures thereof.

When they are present, the total content of cationic polymers in the composition according to the present invention may range from 0.01% to 10% by weight relative to the weight of the composition, preferably from 0.1% to 7% relative to the weight of the composition, even more advantageously from 0.5% to 5% by weight and better still from 0.5% to 3% by weight relative to the weight of the composition.

Carboxylic Acids

The dye composition (A) according to the invention may advantageously comprise one or more carboxylic acids, and/or addition salts thereof and/or solvates thereof, said carboxylic acid(s) being aliphatic compounds, comprising from 2 to 10 carbon atoms and preferably comprising at least two carboxylic groups.

Preferably, they are chosen from aliphatic dicarboxylic and/or tricarboxylic acids comprising from 2 to 10 carbon atoms, preferably from 2 to 8 carbon atoms, better still from 2 to 6 carbon atoms.

In particular, the carboxylic acid(s) are saturated or unsaturated, and substituted or unsubstituted.

Preferably, the carboxylic acids may be chosen from oxalic acid, malonic acid, malic acid, glutamic acid, citraconic acid, citric acid, maleic acid, succinic acid, adipic acid, tartaric acid, fumaric acid, and mixtures thereof.

Preferably, the carboxylic acid(s) comprise at least two carboxylic groups and are chosen from malonic acid, citric acid, maleic acid, glutaric acid, succinic acid, and mixtures thereof; preferably chosen from malonic acid, citric acid, maleic acid, and mixtures thereof.

More particularly preferably, the carboxylic acid is citric acid.

The total content of carboxylic acid(s) and/or addition salts thereof and/or solvates thereof preferably ranges from 0.1% to 20% by weight, relative to the total weight of composition (A).

Preferably, the total content of carboxylic acid(s) ranges from 0.1% to 20%, preferentially from 0.5% to 10% by weight, better still from 1% to 7% by weight, relative to the total weight of the composition, and even better still from 2% to 5% by weight relative to the total weight of composition (A).

Medium

The cosmetically acceptable medium that is suitable for dyeing keratin fibers, also known as a dye support, generally comprises water or a mixture of water and of at least one organic solvent to dissolve the compounds that are not sufficiently water-soluble.

More particularly, the organic solvents are chosen from linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol; glycerol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol monomethyl ether, butylene glycol or dipropylene glycol; and also diethylene glycol alkyl ethers, notably of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

The compositions used according to the invention generally comprise water or a mixture of water and of one or more organic solvents or a mixture of organic solvents.

The composition according to the invention preferably comprises water.

Preferably, the water content ranges from 5% to 95% by weight, more preferentially from 10% to 90% by weight and better still from 20% to 80% by weight relative to the total weight of the composition.

pH of the Medium

The pH of the composition according to the invention generally ranges from 1 to 12. Preferably, the pH of composition (A) according to the invention is basic.

For the purposes of the present invention, the term "basic pH" means a pH above 7.

Preferably, the pH of composition (A) according to the invention is above 8, and particularly ranges from 8.5 to 12.

Preferably, the pH of the composition ranges from 9 to 12.

pH Adjuster

The cosmetically acceptable medium may be adjusted to the desired value by means of acidifying or basifying agents usually used in the dyeing of keratin fibers, or alternatively using standard buffer systems.

Among the acidifying agents, examples that may be mentioned include mineral acids, for instance hydrochloric acid, (ortho)phosphoric acid, boric acid, nitric acid or sulfuric acid, or organic acids, for instance compounds comprising at least one sulfonic acid function, a phosphonic acid function or a phosphoric acid function, or compounds bearing a carboxylic acid function such as those mentioned previously.

Alkaline Agents

According to a preferred embodiment, the composition according to the invention comprises one or more alkaline agents. The alkaline agent(s) (also known as basifying agents) may be mineral, organic and/or hybrid.

Preferably, the composition according to the invention comprises a total content of alkaline agents ranging from 1% to 20% by weight, more preferentially from 3% to 18% by weight and better still from 5% to 16% by weight relative to the total weight of the composition.

According to a first advantageous embodiment of the invention, the alkaline agent(s) are chosen from mineral alkaline agent(s), preferably chosen from aqueous ammonia, also known as ammonium hydroxide (or ammonia precursors such as ammonium salts, for example ammonium halides and in particular ammonium chloride), alkali metal or alkaline-earth metal silicates, phosphates, carbonates or bicarbonates, such as alkali metal or alkaline-earth metal metasilicates, sodium or potassium carbonates or bicarbonates, sodium or potassium hydroxides, or mixtures thereof.

Preferably according to this embodiment, the alkaline agents are chosen from aqueous ammonia (or ammonia precursors such as ammonium salts, for example ammonium halides and in particular ammonium chloride) and/or alkali metal or alkaline-earth metal metasilicates.

According to a preferred embodiment, the alkaline agent(s) are chosen from alkanolamines and/or amino acids.

According to a first preferred embodiment, the alkaline agent(s) are chosen from alkanolamines.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

The compounds of this type are preferably chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane, and mixtures thereof, preferably monoethanolamine (MEA).

According to a second preferred embodiment, the alkaline agent(s) are chosen from amino acids.

As amino acids that may be used in the composition according to the present invention, mention may notably be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Preferably, the alkaline agent(s) present in the composition according to the invention are chosen from aqueous ammonia, alkanolamines and/or amino acids in neutral or ionic form, in particular basic amino acids, preferably arginine, and alkali metal or alkaline-earth metal metasilicates.

Preferably, the composition according to the invention comprises one or more alkaline agents.

According to an advantageous embodiment of the invention, the composition according to the invention comprises:
- one or more mineral alkaline agents, preferably chosen from aqueous ammonia and/or alkali metal or alkaline-earth metal metasilicates, preferably aqueous ammonia; and
- one or more organic agents, preferably chosen from alkanolamines and/or amino acids, preferably from alkanolamines, preferably monoethanolamine.

When the composition comprises aqueous ammonia (ammonium hydroxide), its content preferably ranges from 0.1% to 10% by weight, more preferentially from 0.5% to 8% by weight and better still from 1% to 6% by weight, relative to the total weight of the composition.

When the composition comprises one or more alkanolamines, their total content preferably ranges from 0.5% to 10% by weight, more preferentially from 1% to 9% by weight and better still from 2% to 8% by weight relative to the total weight of the composition.

Other Additives

The composition according to the invention may also contain various additives conventionally used in hair dye compositions, such as mineral thickeners, and in particular fillers such as clays or talc; organic thickeners other than scleroglucan gums; antioxidants; penetrants; sequestrants; fragrances; dispersants; film-forming agents; ceramides; preserving agents; opacifiers; fatty substances and/or additional direct dyes.

The above additives are generally present in an amount for each of them of between 0.01% and 40% by weight relative to the weight of the composition, and preferably between 0.1% and 20% by weight relative to the weight of the composition.

Needless to say, a person skilled in the art will take care to select this or these additional compound(s) such that the advantageous properties intrinsically associated with the composition(s) that are useful in the dyeing process in accordance with the invention are not, or are not substantially, adversely affected by the envisioned addition(s).

Another subject of the invention is a dyeing process using a dye composition (A) as described previously, with an oxidizing composition (B) comprising one or more chemical oxidizing agents.

In particular, the invention is also directed toward a process for dyeing keratin fibers, and in particular human keratin fibers such as the hair, involving the application to the fibers of a dye composition (A) as defined previously, and of an oxidizing composition (B) comprising at least one chemical oxidizing agent, preferably chosen from hydrogen peroxide and/or one or more systems for generating hydrogen peroxide, preferably from hydrogen peroxide, the oxidizing composition (B) being mixed with the dye composition (A) just before use (application to said fibers) (extemporaneously) or at the time of use, or alternatively the dye composition and oxidizing composition being applied sequentially without intermediate rinsing.

Oxidizing Agent:

The oxidizing composition (B) used with the dye composition (A) according to the invention contains one or more chemical oxidizing agents, preferably chosen from hydrogen peroxide and/or one or more systems for generating hydrogen peroxide.

The term "chemical oxidizing agent" means an oxidizing agent other than atmospheric oxygen.

Preferably, the chemical oxidizing agent(s) are chosen from hydrogen peroxide, peroxygenated salts, for instance persulfates, perborates, peracids and precursors thereof, percarbonates of alkali metals or alkaline-earth metals, such as sodium carbonate peroxide, also known as sodium percarbonate and peracids and precursors thereof; alkali metal bromates or ferricyanides, solid hydrogen peroxide-generating chemical oxidizing agents such as urea peroxide and polymer complexes that can release hydrogen peroxide, notably those comprising a heterocyclic vinyl monomer such as polyvinylpyrrolidone/$H_2O_2$ complexes, in particular in powder form; oxidases that produce hydrogen peroxide in the presence of a suitable substrate (for example glucose in the case of glucose oxidase or uric acid with uricase).

Preferably, the chemical oxidizing agent(s) are chosen from hydrogen peroxide, urea peroxide, alkali metal bromates or ferricyanides, peroxygenated salts, and mixtures of these compounds.

Particularly preferably, the chemical oxidizing agent is hydrogen peroxide.

Preferably, the chemical oxidizing agent(s) represent from 0.05% to 40% by weight, preferably from 0.5% to 30% by weight, more preferentially from 1% to 20% by weight and better still from 1.5% to 15% by weight relative to the total weight of the oxidizing composition (B).

Preferably, the oxidizing composition (B) according to the invention does not contain any peroxygenated salts.

As indicated previously, the oxidizing composition (B) comprises one or more scleroglucan gums, preferably in a total content of greater than or equal to 0.5% by weight relative to the weight of the composition.

Preferably, the scleroglucan gum(s) that may be used according to the invention preferably represent from 0.5% to 10% by weight, more preferentially from 0.5% to 5% by weight, even more preferentially from 0.5% to 3% by weight or even from 0.7% to 2% by weight relative to the total weight of the oxidizing composition (B).

The oxidizing composition (B) may also contain various additional compounds or adjuvants conventionally used in compositions for dyeing the hair and notably as defined previously.

The oxidizing composition (B) is generally an aqueous composition. For the purposes of the invention, the term "aqueous composition" means a composition comprising more than 20% by weight of water, preferably more than 30% by weight of water and even more advantageously more than 40% by weight of water.

Preferably, the oxidizing composition (B) usually comprises water, which generally represents from 10% to 98% by weight, preferably from 20% to 96% by weight, preferably from 50% to 95% by weight, relative to the total weight of the composition.

This oxidizing composition (B) may also comprise one or more water-soluble organic solvents as described previously. It may also comprise one or more acidifying agents.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Usually, the pH of composition (B) is less than 7.

The pH of composition (B) of the invention is advantageously between 1 and 7, preferably between 1 and 4 and more preferentially from 1.5 to 3.5.

Finally, the oxidizing composition (B) is in various forms, for instance a solution, an emulsion or a gel.

Dyeing Process

The process of the invention may be performed by applying the dye composition (A) as defined previously and the oxidizing composition (B) successively and without intermediate rinsing, the order being irrelevant.

According to another preferred variant, a ready-to-use composition obtained by extemporaneous mixing, at the time of use, of the dye composition (A) as defined previously and of the oxidizing composition (B) as defined previously is applied to wet or dry keratin materials. According to this embodiment, preferably, the weight ratio R of the amounts of (A)/(B) ranges from 0.1 to 10, preferably from 0.2 to 2 and better still from 0.3 to 1.

In addition, independently of the variant used, the application of the ready-to-use composition to the keratin materials (resulting either from the extemporaneous mixing of the dye composition (A) and the oxidizing composition (B) or from the partial or total successive application thereof) is left in place for a time generally from about 1 minute to 1 hour and preferably from 5 minutes to 30 minutes.

The temperature during the process is conventionally between room temperature (between 15 and 25° C.) and 80° C. and preferably between room temperature and 60° C.

After the treatment, the keratin materials are optionally rinsed with water, optionally subjected to washing followed by rinsing with water, and are then dried or left to dry.

Preferably, the keratin fibers are human keratin fibers, preferably human hair.

A subject of the invention is also a ready-to-use composition for dyeing keratin fibers, in particular human keratin fibers such as the hair, obtained by extemporaneous mixing, at the time of use, of a composition (A) comprising:
  one or more oxidation dyes;
  one or more scleroglucan gums in a total amount of greater than or equal to 0.5% by weight relative to the weight of the composition;
  one or more nonionic surfactants chosen from alkylpolyglycosides;
  and preferably one or more additional surfactants, preferably cationic surfactants;
  and a composition (B) comprising
  one or more a chemical oxidizing agent.

The term "extemporaneous" notably means less than 30 minutes, preferably less than 15 minutes and better still less than 5 minutes before application to the keratin fibers.

According to a particular embodiment of the invention, the chemical oxidizing agent(s) preferably represent a total content ranging from 0.1% to 20% by weight, preferably from 0.5% to 15% by weight or even more preferentially from 1% to 10% by weight relative to the total weight of the ready-to-use composition.

Finally, the invention relates to a multi-compartment device comprising, in a first compartment, a dye composition (A) as described previously, and, in a second, an oxidizing composition (B) comprising one or more oxidizing agents, these compositions having been described previously.

In particular, a subject of the invention is also a multi-compartment device (or "kit") for implementing the composition for dyeing keratin fibers, preferably comprising at least two compartments, a first compartment containing the dye composition (A) as defined previously, and the second compartment containing at least one oxidizing composition (B) comprising at least one chemical oxidizing agent, preferably chosen from hydrogen peroxide and/or one or more systems for generating hydrogen peroxide, preferably from hydrogen peroxide, the compositions in the compartments being intended to be mixed before application, to give the formulation after mixing; in particular, the kit may be an aerosol device.

The examples that follow serve to illustrate the invention without, however, being limiting in nature.

In these examples, the color of the locks was evaluated in the CIE L* a* b* system, using a Datacolor Spectraflash SF600X spectrocolorimeter.

In this L* a* b* system, the three parameters respectively denote the intensity of the color (L*), the green/red color axis (a*) and the blue/yellow color axis (b*). The higher the value of L*, the lighter the color. The higher the value of a*, the redder the color and the higher the value of b*, the yellower the color.

The variation or extent of the dyeing between untreated locks of hair and locks of hair after treatment is defined by the parameter DE* and is calculated according to the following equation:

$$DE^* = \sqrt{(L^*-L_0^*)^2+(a^*-a_0^*)^2+(b^*-b_0^*)^2} \qquad (i)$$

In this equation, the parameters L*, a* and b* represent the values measured on locks of hair after dyeing and the parameters $L_0^*$, $a_0^*$ and $b_0^*$ represent the values measured on locks of untreated hair. The higher the DE* value, the better the dyeing of the keratin fibers.

In the CIE L*, a*, b* system, the chromaticity is calculated according to the following equation:

$$C^* = \sqrt{a^{*2}+b^{*2}}$$

The higher the value of C*, the more chromatic the coloring.

EXAMPLE 1

The following dye compositions were prepared from the following ingredients in the following proportions indicated in grams of active material:

|  | Comp comp C1 outside the invention | Comp comp C2 outside the invention | Comp comp C3 outside the invention | Comp A1 (according to the invention) |
|---|---|---|---|---|
| Ammonium hydroxide | 2.47 | 2.47 | 2.47 | 2.47 |
| Ethanolamine | 4 | 4 | 4 | 4 |
| EDTA | 0.2 | 0.2 | 0.2 | 0.2 |

-continued

|  | Comp comp C1 outside the invention | Comp comp C2 outside the invention | Comp comp C3 outside the invention | Comp A1 (according to the invention) |
|---|---|---|---|---|
| Sodium sulfite | 0.5 | 0.5 | 0.5 | 0.5 |
| Oxidation dyes | 1.401 | 1.401 | 1.401 | 1.401 |
| Fragance | qs | qs | qs | qs |
| Hexadimethrine chloride | 0.3 | 0.3 | 0.3 | 0.3 |
| Polyquaternium-6 | 0.4 | 0.4 | 0.4 | 0.4 |
| Cetylhydroxyethylcellulose | 0.2 | 0.2 | 0.2 | 0.2 |
| Xanthan gum | 1 | — | — | — |
| Algin | — | — | 1 | — |
| Sclerotium gum | — | — | — | 1 |
| Hydroxypropylcellulose | — | 1 | — | — |
| Water | qs 100 | qs 100 | qs 100 | qs 100 |
| Glycerol | 10 | 10 | 10 | 10 |
| Cetrimonium chloride | 0.25 | 0.25 | 0.25 | 0.25 |
| Caprylyl/capryl glucoside | 0.6 | 0.6 | 0.6 | 0.6 |
| Ascorbic acid | 0.4 | 0.4 | 0.4 | 0.4 |

Visual Evaluation of the Stability of the Compositions

The stability of the dye compositions was evaluated by observing the compositions at T0 (immediately after preparation of the composition) and then after 2 months of storage at 45° C.

|  | Composition C1 | Composition C2 | Composition C3 | Composition A1 |
|---|---|---|---|---|
| Observation at T0 at room temperature (25° C.) | Liquid texture Non-homogeneous (phase separation) | Liquid texture Non-homogeneous (phase separation) | Liquid texture Non-homogeneous (phase separation) | Translucent gel Homogeneous (no phase separation) |
| Observation after 2 months at 45° C. | Liquid texture Non-homogeneous (phase separation) | Liquid texture Non-homogeneous (phase separation) | Liquid texture Non-homogeneous (phase separation) | Translucent gel Homogeneous (no phase separation) |

It is observed that composition A1 according to the invention is homogeneous and forms a translucent gel at T0. After 2 months at 45°, composition A1 according to the invention is stable; it is homogeneous and translucent. Comparative compositions $C_1$, $C_2$ and $C_3$ in which the scleroglucan gum was replaced weight-for-weight with another thickener of polysaccharide type are unstable. Specifically, they are not homogeneous; phase separation of these compositions is observed as early as T0.

EXAMPLE 2

The following compositions were prepared from the following ingredients in the following proportions indicated in grams:

|  | Composition A2 according to the invention | Comparative Composition C4 outside the invention |
|---|---|---|
| Ammonium hydroxide | 2.47 | 2.47 |
| Ethanolamine | 4.47 | 4.47 |
| EDTA | 0.2 | 0.2 |
| Sodium sulfite | 0.5 | 0.5 |
| Toluene-2,5-diamine | 0.4 | 0.4 |
| 2-Methyl-5-hydroxyethylaminophenol | 0.264 | 0.264 |
| 4-Amino-2-hydroxytoluene | 1.304 | 1.304 |
| Hydroxyethoxyaminopyrazolopyridine HCl | 1.76 | 1.76 |
| p-Aminophenol | 0.128 | 0.128 |
| Fragance | qs | qs |
| Cetylhydroxyethylcellulose | 0.2 | 0.4 |
| Sclerotium gum | 0.6 | 0.4 |
| Water | qs 100 | qs 100 |
| Glycerol | 10 | 10 |
| Cocoyl betaine | 0.15 | 0.15 |
| Caprylyl/capryl glucoside | 0.6 | 0.6 |
| Ascorbic acid | 0.4 | 0.4 |

Visual Evaluation of the Stability of the Compositions

The stability of the dye compositions was evaluated by observing the compositions at T0 (immediately after preparation of the composition) and then after 2 months of storage at room temperature (25° C.), and after 2 months of storage at 45° C.

|  | Composition A2 according to the invention | Comparative composition C4 |
|---|---|---|
| Observation at T0 (immediately after preparation) | Homogeneous (no phase separation) Texture: Smooth gel | Homogeneous (no phase separation) Texture: Smooth gel |
| Observation after 2 months at 25° C. | Homogeneous (no phase separation) Texture: Smooth gel | Phase separation: Gel with presence of leached liquid |
| Observation after 2 months at 45° C. | Smooth homogeneous gel texture (no phase separation) | Phase separation: Gel with presence of leached liquid |

It is observed that composition A2 according to the invention which comprises a content of scleroglucan gum of greater than or equal to 0.5 by weight relative to the total weight of the composition is stable at room temperature and also at 450 for two months, unlike comparative composition C4 which comprises a content of scleroglucan gum of 0.4% by weight relative to the weight of the composition. Compositions A2 and C4 comprise the same total content of thickener(s) (0.8%). Comparative composition C4 is therefore unstable.

EXAMPLE 3

The following composition was prepared from the following ingredients in the following proportions indicated in grams:

|  | Composition A3 according to the invention |
|---|---|
| Ammonium hydroxide | 1.23 |
| Arginine | 3 |
| Ethanolamine | 5 |
| EDTA | 0.2 |
| Sodium sulfite | 0.5 |
| Citric acid | 3.3 |
| Sodium metasilicate | 2 |
| Toluene-2,5-diamine | 0.16 |
| 4-Amino-2-hydroxytoluene | 0.92 |
| 5-Amino-6-chloro-o-cresol | 0.2 |
| 1-Hydroxyethyl 4,5-diaminopyrazole sulfate | 1.44 |
| p-Aminophenol | 0.12 |
| Fragance | qs |
| Polyquaternium-11 | 1.84 |
| Hexadimethrine chloride | 1.2 |
| Polyquaternium-6 | 0.8 |
| Cetylhydroxyethylcellulose | 0.2 |
| Sclerotium gum | 1 |
| Water | qs 100 |
| Glycerol | 10 |
| Cetrimonium chloride | 0.25 |
| Caprylyl/capryl glucoside | 0.6 |
| Ascorbic acid | 0.4 |

Visual Evaluation of the Stability of the Compositions

The stability of the dye composition was evaluated by observing it at T0 and then after 48 hours at room temperature (25° C.) and then after two months of storage at 45° C.

|  | Composition A3 |
|---|---|
| Observation at T0 (immediately after preparation) at room temperature (25° C.) | Translucent gel Homogeneous (no phase separation) |
| Observation after 2 months at 45° C. | Translucent gel Homogeneous (no phase separation) |

It is observed that composition A3 according to the invention is homogeneous and forms a translucent gel at T0. After two months at 45°, composition A3 according to the invention is stable and in the form of a homogeneous, translucent gel.

EXAMPLE 4

Composition A3 of example 3 was mixed with one times its weight of 20-volumes oxidizing agent (6 g % H2O2 AM). The mixture thus obtained was applied to locks of natural hair containing 90% gray hairs.

The "mixture/lock" bath ratio is, respectively, 10/1 (g/g).

The leave-on time is 30 minutes, on a hotplate set at 27° C. On conclusion of the leave-on time, the locks are rinsed and then dried under a drying hood at 40° C.

The color of the locks was evaluated in the CIE L* a* b* system, using a Datacolor Spectraflash SF600X spectrocolorimeter.

|  | a* | b* | C* |
|---|---|---|---|
| Coloring obtained with the mixture of composition A3 + oxidizing agent | 21.40 | 10.03 | 23.63 |

Chromatic coloring of the keratin fibers is obtained.

The invention claimed is:

1. A composition for dyeing keratin fibers, comprising:
   at least one oxidation dye;
   at least one scleroglucan gum in a total weight content of greater than or equal to 0.5% by weight, relative to the total weight of the composition; and
   at least one nonionic surfactant chosen from alkylpolyglycosides.

2. The composition of claim 1, wherein the at least one scleroglucan gum is present in an amount ranging from 0.5% to 10% by weight, relative to the total weight of the composition.

3. The composition of claim 1, wherein the at least one oxidation dye is chosen from benzene-based oxidation bases, or salts thereof, wherein the at least one oxidation dye is optionally combined with at least one coupler chosen from meta-phenylenediamines, meta-aminophenols, meta-diphenols, naphthalene-based couplers, heterocyclic couplers, or salts thereof.

4. The composition of claim 1, wherein the at least one oxidation dye is chosen from para-phenylenediamines, bis (phenyl)alkylenediamines, para-aminophenols, ortho-aminophenols, heterocyclic bases, or salts thereof.

5. The composition of claim 1, wherein the at least one nonionic surfactant chosen from alkylpolyglucosides is chosen from compounds of the following general formula:

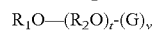

wherein:
R$_1$ is chosen from a linear or branched alkyl or alkenyl radical including 6 to 24 carbon atoms, or an alkylphenyl radical comprising a linear or branched alkyl radical including 6 to 24 carbon atoms;

R₂ is chosen from an alkylene radical including 2 to 4 carbon atoms;

G represents a sugar unit including 5 to 6 carbon atoms;

t denotes a value ranging from 0 to 10; and v denotes a value ranging from 1 to 15.

6. The composition of claim 5,
wherein in the compounds of formula $R_1O—(R_2O)_t-(G)_v$, R₁ is chosen from a linear or branched, saturated or unsaturated alkyl radical including from 8 to 18 carbon atoms;

R₂ represents an alkylene radical including 2 to 4 carbon atoms;

t denotes a value ranging from 0 to 3; and

G is chosen from glucose, fructose, or galactose; and v denotes a value ranging from 1 to 4.

7. The composition of claim 1, wherein the at least one nonionic surfactant chosen from alkylpolyglucosides is chosen from ($C_6$-$C_{24}$ alkyl)(poly)glycosides.

8. The composition of claim 7, wherein the at least one nonionic surfactant chosen from alkylpolyglucosides is chosen from decyl glucosides, cocoyl glucosides, or caprylyl/capryl glucosides.

9. The composition of claim 1, wherein the at least one nonionic surfactant chosen from alkylpolyglycosides is present in a total amount ranging from 0.01% to 10% by weight, relative to the total weight of the composition.

10. The composition of claim 1, further comprising at least one additional surfactant other than alkyl(poly)glycosides.

11. The composition of claim 10, wherein the at least one additional surfactant is chosen from cationic surfactants comprising cetyltrimethylammonium salt, behenyltrimethylammonium salt, dipalmitoylethylhydroxyethylmethylammonium salt, or a mixture thereof.

12. The composition of claim 1, further comprising at least one nonionic associative polymer; wherein the at least one nonionic associative polymer is present in a total amount ranging from 0.01% and 10% by weight, relative to the total weight of the composition.

13. The composition of claim 12, wherein the at least one nonionic associative polymer is chosen from celluloses modified with groups including at least one fatty chain.

14. The composition of claim 1, further comprising at least one carboxylic acid, a salt thereof, a solvate thereof, or a mixture thereof, being present in an amount ranging from 1% to 10% by weight, relative to the total weight of the composition.

15. The composition of claim 1, further comprising at least one alkaline agent.

16. The composition of claim 15, wherein the at least one alkaline agent is chosen from aqueous ammonia, alkali metal, or alkaline-earth metal metasilicates, alkanolamines, amino acids, or mixtures thereof.

17. The composition of claim 1, further comprising at least one chemical oxidizing agent.

18. The composition of claim 17, wherein the at least one chemical oxidizing agent is chosen from hydrogen peroxide, or at least one system generating hydrogen peroxide.

19. A method for dyeing keratin fibers, comprising applying to the keratin fibers a dye composition (A) and an oxidizing composition (B), wherein:

the dye composition (A) comprises:

at least one oxidation dye;

at least one scleroglucan gum in a total weight content of greater than or equal to 0.5% by weight relative to the total weight of the dye composition (A); and at least one nonionic surfactant chosen from alkylpolyglycosides;

the oxidizing composition (B) comprises at least one chemical oxidizing agent; and the oxidizing composition (B) is extemporaneously mixed with the dye composition (A) just before being applied to the keratin fibers, or alternatively, the dye composition (A) and the oxidizing composition(B) are applied sequentially to the keratin fibers without intermediate rinsing.

20. A multi-compartment kit comprising:

a first compartment containing a dye composition (A) comprising;

at least one oxidation dye;

at least one scleroglucan gum in a total weight content of greater than or equal to 0.5% by weight relative to the total weight of the dye composition (A); and at least one nonionic surfactant chosen from alkylpolyglycosides; and a second compartment containing an oxidizing composition comprising at least one chemical oxidizing agent.

\* \* \* \* \*